US010557844B2

(12) United States Patent
Keays

(10) Patent No.: US 10,557,844 B2
(45) Date of Patent: Feb. 11, 2020

(54) BIORESISTIVE-FINGERPRINT BASED SOBRIETY MONITORING SYSTEM

(71) Applicant: SOBERLINK HEALTHCARE, LLC, Huntingdon Beach, CA (US)

(72) Inventor: Brad Keays, Manhattan Beach, CA (US)

(73) Assignee: SOBERLINK HEALTHCARE, LLC, Huntington Beach, CA (US)

(*) Notice: Subject to any disclaimer, the term of this patent is extended or adjusted under 35 U.S.C. 154(b) by 230 days.

(21) Appl. No.: 15/483,196

(22) Filed: Apr. 10, 2017

(65) Prior Publication Data
US 2017/0336388 A1 Nov. 23, 2017

Related U.S. Application Data

(60) Provisional application No. 62/320,245, filed on Apr. 8, 2016.

(51) Int. Cl.
B60K 28/00 (2006.01)
G01N 33/497 (2006.01)
B60K 28/06 (2006.01)
G08B 21/02 (2006.01)
A61B 5/08 (2006.01)
A61B 5/00 (2006.01)

(52) U.S. Cl.
CPC ......... *G01N 33/4972* (2013.01); *A61B 5/082* (2013.01); *A61B 5/4845* (2013.01); *B60K 28/063* (2013.01); *G08B 21/02* (2013.01)

(58) Field of Classification Search
CPC .............. G01N 33/4972; B60K 28/063; A61B 5/4845; A61B 5/082; G08B 21/02

USPC .......................................... 180/272; 73/23.3
See application file for complete search history.

(56) References Cited

U.S. PATENT DOCUMENTS

| 3,437,449 | A  | 4/1969 | Luckey |
| 4,093,945 | A  | 6/1978 | Collier et al. |
| 4,132,109 | A  | 1/1979 | VanderSyde |
| 4,564,021 | A  | 1/1986 | Siegmann et al. |
| 4,843,377 | A  | 6/1989 | Fuller et al. |
| 5,220,919 | A  | 6/1993 | Phillips et al. |
| 6,026,674 | A  | 2/2000 | Gammenthaler |
| 6,726,636 | B2 | 4/2004 | Der Ghazarian et al. |

(Continued)

FOREIGN PATENT DOCUMENTS

WO  WO 2008/076310 A1  6/2008

OTHER PUBLICATIONS

CA, 2,780,108 Office Action, dated Mar. 31, 2015.
(Continued)

*Primary Examiner* — Toan C To
(74) *Attorney, Agent, or Firm* — One LLP; Joseph K. Liu

(57) ABSTRACT

A system for communicating the sobriety of a user that includes a testing device that generates a substance content signal comprising a mouthpiece and a user identification device, wherein the substance content signal comprises at least one substance information, wherein the user identification device generates user identification data in response to a user's breath and transmits it from the testing device to a monitoring station, and wherein the testing device further comprises at least one of a LCD screen or a LED; a transceiver unit; a receiving station; and a supervisory monitor.

3 Claims, 6 Drawing Sheets

(56) References Cited

U.S. PATENT DOCUMENTS

| | | | |
|---|---|---|---|
| 6,748,792 B1* | 6/2004 | Freund | B60K 28/063 180/272 |
| 6,837,095 B2 | 1/2005 | Sunshine et al. | |
| 6,899,683 B2 | 5/2005 | Mault et al. | |
| 7,341,693 B2 | 3/2008 | Der Ghazarian et al. | |
| 7,462,149 B2 | 12/2008 | Hawthorne et al. | |
| 7,611,461 B2 | 11/2009 | Hawthorne et al. | |
| 7,636,047 B1 | 12/2009 | Sempek | |
| 7,641,611 B2 | 1/2010 | Hawthorne et al. | |
| 7,833,166 B2 | 11/2010 | Ruffert | |
| 7,841,224 B2 | 11/2010 | Son | |
| 7,934,577 B2 | 5/2011 | Walter et al. | |
| 8,249,311 B2 | 8/2012 | Endo et al. | |
| 8,280,436 B2 | 10/2012 | Harris, Jr. | |
| 8,381,573 B2 | 2/2013 | Keays | |
| 8,707,758 B2 | 4/2014 | Keays | |
| 9,228,997 B2 | 1/2016 | Keays | |
| 9,239,323 B2 | 1/2016 | Keays | |
| 9,707,845 B1* | 7/2017 | Nienhouse | H04Q 9/00 |
| 10,034,635 B2* | 7/2018 | Nothacker | A61B 5/082 |
| 10,352,923 B2* | 7/2019 | Nothacker | G01N 33/4972 |
| 2002/0084130 A1 | 7/2002 | Der Ghazarian et al. | |
| 2002/0127145 A1* | 9/2002 | Der Ghazarian | A61B 5/083 422/83 |
| 2002/0177232 A1 | 11/2002 | Melker et al. | |
| 2003/0004403 A1 | 1/2003 | Drinan et al. | |
| 2004/0236199 A1 | 11/2004 | Hawthorne et al. | |
| 2004/0239510 A1* | 12/2004 | Karsten | B60K 28/063 340/576 |
| 2005/0065446 A1 | 3/2005 | Talton | |
| 2006/0009257 A1 | 1/2006 | Ku | |
| 2006/0202838 A1 | 9/2006 | Hawthorne et al. | |
| 2007/0016092 A1 | 1/2007 | Shaw et al. | |
| 2007/0062255 A1 | 3/2007 | Talton | |
| 2007/0144812 A1* | 6/2007 | Stewart | B60K 28/063 180/272 |
| 2007/0239992 A1 | 10/2007 | White et al. | |
| 2007/0258894 A1 | 11/2007 | Melker et al. | |
| 2007/0261468 A1 | 11/2007 | Crespo et al. | |
| 2008/0009693 A1 | 1/2008 | Hawthorne et al. | |
| 2008/0183502 A1 | 7/2008 | Dicks et al. | |
| 2008/0314115 A1 | 12/2008 | Faulder et al. | |
| 2009/0053110 A1 | 2/2009 | Chanq et al. | |
| 2009/0060287 A1* | 3/2009 | Hyde | A61B 5/0002 382/118 |
| 2009/0182216 A1 | 7/2009 | Roushev, III et al. | |
| 2009/0201138 A1 | 8/2009 | Ghazarian et al. | |
| 2009/0293589 A1* | 12/2009 | Freund | G07C 5/0891 73/23.3 |
| 2010/0012417 A1* | 1/2010 | Walter | B60K 28/063 180/272 |
| 2010/0089121 A1 | 4/2010 | Hemmingsson et al. | |
| 2010/0138166 A1 | 6/2010 | Do et al. | |
| 2010/0204600 A1 | 8/2010 | Crucilla | |
| 2010/0251804 A1 | 10/2010 | Morley et al. | |
| 2012/0031166 A1 | 2/2012 | Lopez et al. | |
| 2012/0242469 A1* | 9/2012 | Morgan | B60K 28/06 340/426.11 |
| 2012/0302907 A1 | 11/2012 | Palmskog et al. | |
| 2013/0006068 A1 | 1/2013 | Gemer et al. | |
| 2014/0041436 A1 | 2/2014 | Knott et al. | |
| 2014/0311215 A1 | 10/2014 | Keays et al. | |
| 2015/0084774 A1 | 3/2015 | Wojcik et al. | |
| 2018/0101721 A1* | 4/2018 | Nienhouse | G06K 9/00288 |

OTHER PUBLICATIONS

WO, PCT/US2010/050930 ISR and Written Opinion, dated Dec. 2, 2010.

WO, PCT/US2014/029411 ISR and Written Opinion, dated Jul. 28, 2014.

WO, PCT/US2015/064570 ISR and Written Opinion, dated Feb. 11, 2016.

Ahlber, P. "Electronic Nose Offers Food Processors a Powerful New Smell Identification Tool," Food Online. Mar. 13, 2000. Accessed online <http://www.foodonline.com> on Jul. 29, 2013.

Angell, L.C., "iBreath iPod add-on features alcohol breathalyzer," <http://www.ilounge.com>, published online Sep. 11, 2006.

Berchtold, C., et al., "Evaluation of extractive electrospray ionization and atmospheric pressure chemical ionization for the detection of narcotics in breath", International Journal of Mass Spectrometry, 2011, vol. 299, pp. 145-150.

CNET Reviews, "iBreath: the iPhone Breathalyzer," <http://reviews.cnet.com>, published online on Dec. 15, 2008.

Fariva, C., "iBreath, your iPod-powered breathalyzer," <http://www.engadget.com>, published online on Sep. 12, 2006.

"Hand-held Analytical Power for Workplace Monitoring," News Release from Quantitech Ltd, Jul. 2, 2004. Accessed on line on Jul. 29, 2013 at <http://www.edie.net/news/O/Hand-held-Analytical-Power-for-Workplace-Monitoring/8540/>.

Manolis, A., "The Diagnostic Potential of Breath Analysis," Clin. Chem. 29/1, pp. 5-15 (1983).

Millward, D., "Motorists face roadside drug tests under government plans," Telegraph. May 10, 2009.

Millward, D., "Roadside drug testing device developed by academics," Telegraph. Nov. 15, 2011.

Mullett, G., Wireless Telecommunications Systems and Networks (Thomson 2006).

"New technique enables drugs tests via exhaled breath", Karolinska Institutet, 2010, retrieved from < http://www.sciencedaily.com/releases/2010/05/100519081438.htm> on Jul. 22, 2015.

http://www.intoxalock.com/intoxalock-alcohol-monitoring-systems.cfm (printed at least as early as Oct. 15, 2012).

http://www.web.archive.org/web/20090311081549/http://alcoholmonitoring.com/index/scram/what-is-scram (printed at least as early as Oct. 15, 2012).

Electronic Monitoring System, MEMS 3000 Homestation Installation Guide, Elmo Tech Ltd., Mar. 2006.

Intoxalock Overview: Mobile eLERT Camera, <http://intoxalock.com/mobile-elert-camera.cfm>, print date: Dec. 4, 2012.

IPR2013-00577 (Paper 5), Amended Petition for Inter Partes Review (Sep. 20, 2013).

IPR2013-00577 (Paper 10), Preliminary Response (Dec. 9, 2013).

IPR2013-00577 (Paper 12), Institution Decision (Feb. 13, 2014).

IPR2013-00577 (Paper 22), Patent Owner Response (May 7, 2014).

IPR2013-00577 (Paper 26), Petitioner Reply (Jul. 21, 2014).

IPR2013-00577 (Paper 40), Final Decision (Jan. 13, 2015).

IPR2013-00577 (Ex. 1019), Decl. of McAlexander III (Sep. 9, 2013).

IPR2013-00577 (Ex. 1020), Decl. of McAlexander III, continued (Sep. 9, 2013).

IPR2015-00556 (Paper 2), Petition for Inter Partes Review (Jan. 12, 2015).

IPR2015-00556 (Paper 7), Decision Institution of Inter Partes Review (Jul. 16, 2015).

IPR2015-00556 (Ex. 1104), "MEMS 3000 Homestation Installation Guide," ElmoTech, Ltd. (Mar. 2006).

IPR2015-00556 (Ex. 1107), Borkenstien & Smith, "The Breathalyzer and its Application," 2 Medicine, Science, and the Law 13 (1962).

IPR2015-00556 (Ex. 1116), Depo. Tr. of Dr. Skipper, (Jun. 25, 2014).

IPR2015-00556 (Ex. 1124), Decl. of Wojcik, (Jan. 12, 2015).

IPR2015-00556 (Ex. 1130), Paul Diggan, "Long Arm of the Law has Man by the Ankle," Washington Post (Mar. 18, 2005).

IPR2015-00556 (Ex. 1131), Wayback Machine Archive: www.bi.com/sobrietor (accessed: Nov. 15, 2014).

IPR2015-00556 (Ex. 1132), Mike Hanlon, "The LG Breathalyzer Phone," Gizmag (Jul. 7, 2006).

IPR2015-00556 (Ex. 1133), CNET Staff, "iBreath: the iPhone Breathalyzer," CNET (Dec. 14, 2008).

IPR2015-00556 (Ex. 1134), Wayback Machine Archive: www.sentalt.com/vicap.htm (accessed: Nov. 15, 2014).

IPR2015-00556 (Ex. 1135), "Program monitors alcohol-related offenders," Rapid City Journal (Feb. 29, 2004).

(56) References Cited

OTHER PUBLICATIONS

IPR2015-00556 (Ex. 1136), Wayback Machine Archive: www.isecuretrac.com/services.aspx?p=alcoholmonitoring (accessed: Nov. 15, 2014).
IPR2015-00556 (Ex. 1137), "MEMS 3000 Cellular Receiver and Transmitter Installation Guide," ElmoTech, Ltd. (submitted on Jan. 12, 2015).
IPR2015-00556 (Ex. 1138), Wayback Machine Archive: www.spartstartinc.com/index.php/products/in-house (accessed: Nov. 17, 2014).
IPR2015-00556 (Ex. 1139), Wayback Machine Archive: www.streetimetechnolgies.com/products/mobilebreath (accessed: Dec. 9, 2014).
IPR2015-00556 (Ex. 1141), Wayback Machine Archive: http://tsc.trackingsystemscorp.com/mem4.htm (accessed: Nov. 17, 2014).
IPR2015-00556 (Ex. 1142), "MEMS 3000 Homestation & Transmitter Installation Guide," ElmoTech, Ltd. (Sep. 2005).
IPR2015-00556 (Ex. 1143), Editorial Staff, "LifeSafer Interlock Launches the Portable and Home Alcohol Monitoring System," LifeSafer (Jun. 15, 2011).
IPR2015-00556 (Ex. 1144), Douglass Martin, "Robert F. Borkenstein, 89, Inventor of the Breathalyzer," New York Times (Aug. 17, 2002).
IPR2015-00556 (Ex. 1145), "iSECUREtrac In-home Alcohol Testing," iSECUREtrac (submitted on Jan. 12, 2015).
IPR2015-00556 (Ex. 1146), "Electronic Home Monitoring Services Offered by Alternative Corrections, Inc.," Alternative Corrections, Inc. (submitted on Jan. 12, 2015).
IPR2015-00556 (Ex. 1147), Wayback Machine Archive: www.alertinc.us/electronic_monitoring_equipment.htm (accessed: Nov. 24, 2014).
IPR2015-00556 (Ex. 1148), Wayback Machine Archive: www.questguard.com/Breathalyzer-Testing_.html (accessed: Nov. 11, 2014).
IPR2015-00556 (Ex. 1149), Dept. Transp., "Highway Safety Programs; Conforming Products List of Screening Devices to Measure Alcohol in Bodily Fluids," 59 Fed. Reg. 231 (Dec. 2, 1994).
IPR2015-00556 (Ex. 1150), Dept. Transp., "Highway Safety Programs; Conforming Products List of Screening Devices to Measure Alcohol in Bodily Fluids," 47 Fed. Reg. 239 (Dec. 15, 2009).
IPR2015-00556 (Ex. 1151), Globes Corresp., "Dmatek buys Mitsubishi's alcohol monitoring product line," Globes Israel's Business Arena (Sep. 12, 2002).
IPR2015-00556 (Ex. 1152), "BTI2 Electrical Specifications," Alcohol Countermeasure Systems (Sep. 29, 2004).
IPR2015-00556 (Ex. 1153), "MEMS 3000 GSM Operational Description," ElmoTech, Ltd. (submitted on Jan. 12, 2015).
IPR2015-00556 (Ex. 1154), "MEMS 3000 GSM Block Diagram," ElmoTech, Ltd. (submitted on Jan. 12, 2015).
Website: http://www.tokai-denshi.com/english/products/ALC-Mobile_1.html (accessed: Jul. 30, 2014).
Website: http://www.tokai-denshi.com/english/products/ALC-Mobile_3-1.html (accessed: Jul. 30, 2014).
Website: http://www.lifesafer.com/blog/lifesafer-interlock-launches-the-portable-and-home-alcohol-monitoring-system/ (accessed: Aug. 1, 2014).
Website: http://www.prnewswire.com/newsreleases/lifesafer-interlock-launches-the-portable-and-home-alcohol-monitoring-system-124662013.html (accessed: Aug. 1, 2014).
Website: http://www.smartstartinc.com/repository/nov2011-press-release/ (accessed: Aug. 1, 2014).
Website: http://www.eramonitoring.com/products_Mems3000.html (accessed: Aug. 1, 2014).
Website: http://web.archive.org/web/20081210155459/http://www.isecuretrac.com/services.aspx?p=alcoholmonitoring (accessed: Aug. 1, 2014).
Website: http://www.corrections.com/articles/11251-vi-cap-videoinformation-capture (accessed: Aug. 1, 2014).
Website: http://www.mobileinc.co.uk/2009/07/one-you-may-have-missed-the-lg-breathalyzer-phone/ (accessed: Aug. 1, 2014).
Website: http://www.smartstartinc.com/about-us/ (accessed: Aug. 1, 2014).
Website: http://www.smartstartinc.com/wpcontent/uploads/2014/04/Smart_Start_App_April_11_Final_Release.pdf (accessed: Aug. 1, 2014).
Website: http://www.webarchive.org/web/20110627002850/http://www.lifesafer.com/hmu.php (accessed: Aug. 1, 2014).
Website: http://www.webarchive.org/web/2011061122248/http://www.streetimetechnologies.com/products/mobilebreath (accessed: Aug. 1, 2014).
Website: http://bi.com/node/483 (accessed: Aug. 1, 2014).

* cited by examiner

BIORESISTIVE-FINGERPRINT BASED SOBRIETY MONITORING SYSTEM

CROSS-REFERENCE TO RELATED APPLICATIONS

The present application claims benefit of priority with U.S. Provisional Application No. 62/320,245, filed Apr. 8, 2016, which is hereby incorporated by reference.

TECHNICAL FIELD

This disclosure relates generally to a system for remote sobriety monitoring, and more particularly relates to a system utilizing a testing device for analyzing the alcohol content or other substance content of the breath of a user in combination with a wireless or cellular transmitter or transceiver to transmit an alcohol content or other substance content signal to a wireless or cellular device and/or monitoring station to help ensure abstinence of the user from the use of alcohol or another substance.

BACKGROUND OF THE INVENTION

One of the challenges in remotely monitoring someone's sobriety with a mobile breathalyzer is being able to say with certainty that a person being monitored was the one taking the breath test. Some current state of the art devices use an integrated digital imager to take a photograph of the user as they blow into the device, and also rely on breath temperature and pressure sensors to determine if an air source other than the user's breath is being used. These devices were described in U.S. patent application Ser. No. 13/357,494 (which is now U.S. Pat. No. 8,707,758, to Keays), U.S. patent application Ser. No. 13/274,553 (which is now U.S. Pat. No. 9,228,997, to Keays), U.S. patent application Ser. No. 12/882,323 (which is now U.S. Pat. No. 8,381,573, to Keays), and U.S. patent application Ser. No. 14/199,690 (which is now U.S. Pat. No. 9,239,323, to Keays), the contents and disclosures of which are herein incorporated by reference. This works well. However, the use of a digital imager presents several issues that are less than desirable. Because the imager is typically close to the user's face when they blow into the device, a wide-angle lens is used to capture an image of the whole face. This results in an image with a "fish eye" effect, making the user hard to recognize.

It would therefore be desirable to provide a method and system of providing a system and method for monitoring sobriety that is portable, effective, and including externally visible identification indicia that can be used to positively identify the user. The present invention meets these and other needs.

SUMMARY OF THE INVENTION

Briefly, and in general terms, the present invention provides for a system and method for monitoring sobriety of a user on an automated basis, utilizing a hand-held breath testing and identification device ("testing device"), a wireless or cellular transmitter or transceiver device for wirelessly transmitting results of the breath testing to a wireless or cellular receiver monitoring station. The monitoring station receives the breath testing results including a randomly generated identification indicia from the wireless or cellular transmitter or transceiver device.

In some embodiments, the monitoring station may indicate an alarm or otherwise alert an on-call monitor when the wireless or cellular transmitter or transceiver is indicated to be off, or when the breath testing results indicate a substance content greater than a predetermined threshold, or when the received breath is not the breath of the user, for example, as determined by using at least a randomly generated identification indicia as described herein in more detail.

The system and method can also be used in connection with a traditional sober buddy, chaperone service on an on-call basis, to limit the expense and labor intensiveness of the supervisory care. Such systems may also be used to monitor abstinence from other drugs, which can be taken orally and tested by a breath analyzer or the like without the use of a chaperone on a continuing basis.

A cellular module can alternatively be integrated with the testing device that can send a breath test report and identification data directly through WiFi, cell towers, or through other mobile wireless networks such as those that do not rely on fixed infrastructure.

An external mobile device, such as a device coupled to a smart phone or a tablet, or a smart phone or a tablet, and the like, may be used in synchronization with the testing device to capture a photograph of the user and the testing and identification device while the test is in progress, and transmitting the photograph to the monitoring station.

These and other aspects and advantages of the invention will be apparent from the following detailed description and the accompanying drawings, which illustrate by way of example the features of the invention.

BRIEF DESCRIPTION OF THE DRAWINGS

Illustrated in the accompanying drawings is at least one of the best mode embodiments of the present invention In such drawings.

DETAILED DESCRIPTION OF THE INVENTION

Figure 1:
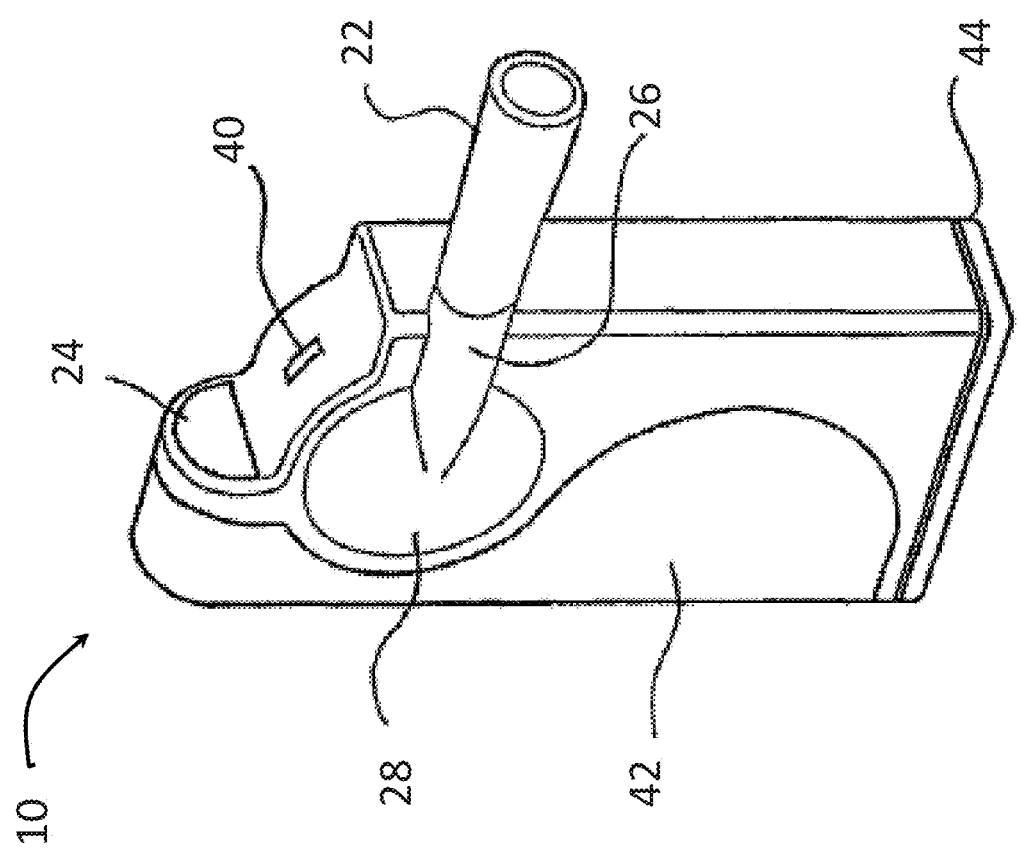
FIG. 1 illustrates a perspective view of a testing device for monitoring sobriety, according to an embodiment of the invention.

The above described figures illustrate the described apparatus and its method of use in at least one of its preferred, best mode embodiments, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

In the following description and in the figures, like elements are identified with like reference numerals. The use of "e.g.," "etc," and "or" indicates non-exclusive alternatives without limitation, unless otherwise noted. The use of "including" or "includes" means "including, but not limited to," or "includes, but not limited to," unless otherwise noted.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B", when used in conjunction with open-ended language such as "comprising" can refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

Described now in detail are systems and methods for monitoring sobriety of a user as a way to prevent the user from consuming further alcohol or another substance, or as an intermediate, automated way of engaging the services of a sober buddy, sober companion, sober coach, or other supervisory care for the user to help ensure against relapse of the user, and to help the user maintain sufficient abstinence from alcohol or another substance to reside and function outside of a treatment facility.

In some embodiments, a testing device (or breathalyzer) communicates with a mobile device of a user, such as a smartphone, to send a blood-alcohol content ("BAC") of the user to the mobile device after the testing device completes the test. In some other embodiments, the testing device may also communicate with the mobile device while the test is in progress, and the mobile device takes a photograph of the user. It is said that this way, the BAC of the user can be verified as that of the user in the photograph, for example, when the BAC and the photograph are sent to a monitoring system, or when the BAC is sent to the mobile device. However, a user could simply find a way to have a breathalyzer of another user, who is sober, to send a BAC of the other sober user to the mobile device of the user. For example, the mobile device of the user takes a photograph of the user but receives the BAC of the sober user while the sober user blows into the breathalyzer of the other user. As a result, the BAC of the other sober user is associated with the photograph of the user, who may not be sober. This and other tampering schemes render the testing unreliable.

To solve these problems, a visible identification indicia integrated with the testing device is proposed. A visible identification indicia is generated synchronously, or substantially synchronously, with the capturing of the user's breath and BAC calculation as the user blows into the testing device. The visible identification indicia is also simultaneously, or substantially simultaneously, recorded as associated with the BAC of the user. As such, when a mobile device captures a photograph of the user using the testing device, it will also capture the visible identification indicia. As a result, in order to positively verify that the user of the testing device is the actual user in the captured photograph, the visible identification indicia captured in the photograph must match the visible identification indicia recorded with the BAC.

In some embodiments, the visible identification indicia may be a random number, for example, from 0 to 9. Other ranges of random numbers, or random number series are also contemplated. Such visible identification indicia may be displayed on a display screen, for example, a liquid crystal display ("LCD") screen, of the testing device. In some embodiments, the visible identification indicia may be a random color, or color scheme. Such visible identification indicia may be displayed on a display screen, or by a light-emitting diode ("LED"), or a suitable light source on the testing device. In other embodiments, the visible identification indicia may include both a random number (or random number series) and a random color (or a color scheme). Other randomly generated visible identification indicia are also contemplated.

Figure 3:
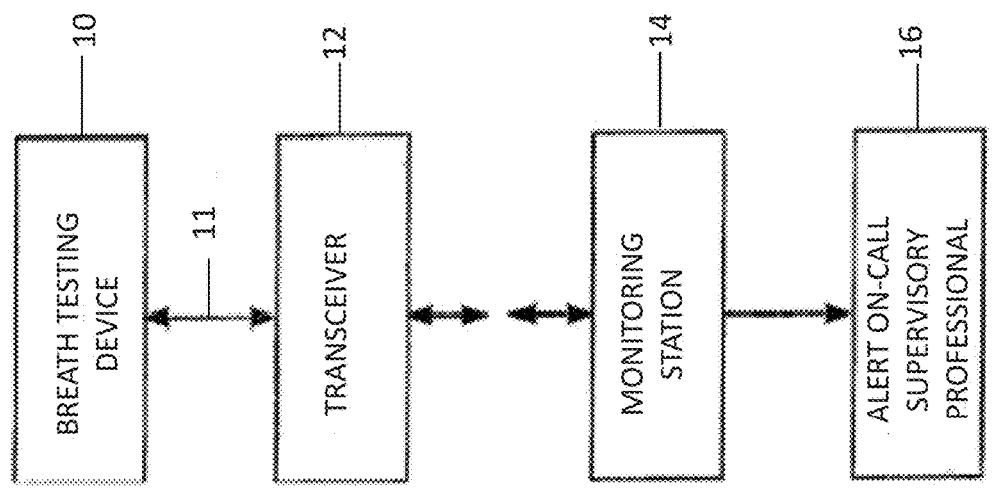
FIG. 3 illustrates a schematic diagram of a method and system for monitoring sobriety, according an embodiment of the invention.

Referring to FIG. 1, a perspective view of an exemplary embodiment of a testing device 10 (which may also be referred to herein as a breathalyzer) is shown. In this example, the testing device 10 is a handheld device operable to test the presence of alcohol or other substance in the breath of the user. Additionally, the testing device 10 is preferably operable to generate a substance content signal 11 (as shown in FIG. 3) comprising at least one substance content information. For example, the testing device 10 may include a breathalyzer-type testing device operable to analyze the alcohol content of the breath of a user and generate an alcohol content signal indicative of the alcohol content of the user's breath.

The testing device 10 may include a mouthpiece 22 and user identification device ("UID") 24. The UID 24 is operable to generate user identification data. In some embodiments, the UID 24 may be a fingerprint reader or a camera that generates identification data while the test is in progress. Thus, the substance content signal 11 may also include one or more user identification data. The testing device 10 may include a status LED 40, such as for indicating when the device is ready for use and when the device has completed breath testing and identification. The mouthpiece 22 may be removably mounted to an end of an extension portion 26, which is in turn connected to a breath analysis and processing portion 28 of the testing device 10.

The testing device 10 may also include an over mold grip portion 42, a battery door 44 for installing and maintaining or recharging batteries (not shown) for powering operation of the device and a breath sensor (not shown) of the device.

Figure 2B:
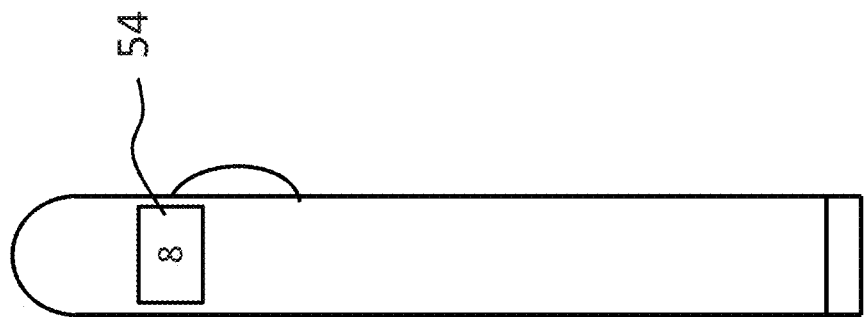
FIG. 2B illustrates a rear view of a testing device for monitoring sobriety of FIG. 1 including an LCD for displaying identification indicia, according to an embodiment of the invention.
Figure 2A:
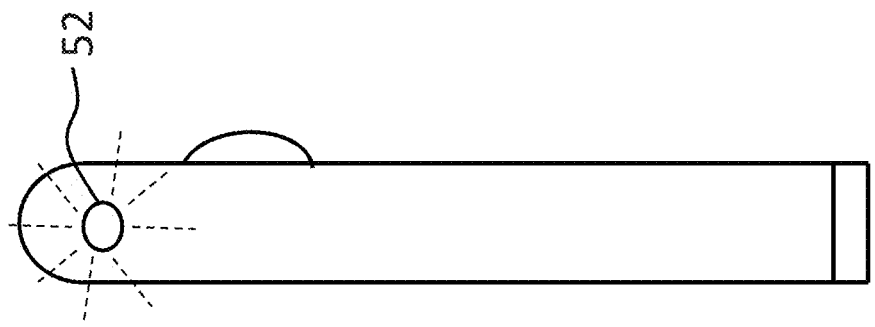
FIG. 2A illustrates a rear view of a testing device for monitoring sobriety of FIG. 1 including an LED for displaying identification indicia, according to an embodiment of the invention.

Referring to FIG. 2A, a rear view of an exemplary embodiment of the testing device 10 is shown. In some embodiments, the testing device 10 may include an LED 52 for generating visible identification indicia. The testing device 10 may generate a random color or a color scheme while the test is in progress. The randomly generated color or color scheme is displayed using the LED 52 and may be included in the substance content signal 11 (as shown in FIG. 3) as user identification data. As described herein, the user and the rear view of the testing device 10 showing the randomly generated color or color scheme may be photographed by a mobile device connected, for example, wirelessly, to the testing device 10 while the test is in progress.

Referring to FIG. 2B, another rear view of an exemplary embodiment of the testing device 10 is shown. In some embodiments, the testing device 10 may include an LCD display 54 for generating visible identification indicia. The testing device 10 generates a random number, for example, from 0 to 9, while the test is in progress. The randomly generated number may be displayed on the LCD display 54 (e.g., randomly generated number 8 is shown in FIG. 2B) and also included in the substance content signal 11 as user identification data. Other ranges of random numbers or random number series are also contemplated. As described herein, the user and the rear view of the testing device 10 showing the randomly generated number may be photographed by a mobile device connected, for example, wirelessly, to the testing device 10 while the test is in progress. It is noted that other types of randomly generated visible identification indicia using the LED 52 or the LCD 54, or both, are also contemplated.

Referring to FIG. 3, in an exemplary embodiment, a testing device 10, a transceiver unit 12, a receiving station 14, and a supervisory monitor 16 may be provided. The transceiver unit 12 may be configured to transmit the content signal 11 to the receiving station 14. The substance content signal 11 may also include user identification data. Alternatively, the user identification data may be transmitted to the receiving station 14 separately from the content signal 11. In at least one embodiment, the content signal 11 includes a digitized report that may be accessible by a supervisory monitor 16. Transmission may occur over a wireless, wired, cellular, or any other type of network now known or hereafter developed. In at least one embodiment, the transceiver unit 12 is internal to the testing device 10 and is a hardware component thereof.

The receiving station 14 may be configured to receive the content signal 11. The receiving station 14 may be configured to inform the supervisory monitor 16 if the content signal 11 is not received from the transceiver at a predetermined time, or if the content signal 11 indicates that the substance content levels exceed a predetermined threshold. For example, the typical legal limit of blood alcohol content (BAC) is 0.08%. Thus, the receiving station may inform the supervisory monitor 16 if the content signal indicates the user's BAC is greater than 0.08%. Importantly, the predetermined threshold may be set at a higher or lower level as may be desired. Additionally, the receiving station 14 may be configured to convey the content signal 11, or a report based thereon, directly to the supervisory monitor 16 so that the supervisory monitor 16 is made aware of the substance information. Thus, for example, the receiving station may inform the supervisory monitor 16 (who may be a parent or guardian) that the user (who may be a teenage child of the parent or guardian) has a BAC of 0.03%.

In some embodiments, the receiving station 14 may include any location, device, or system where the content signal 11 is received, including, for example: a monitoring station, a cellular/smart phone, an email account, a website, a network database, and a memory device. Additionally, the supervisory monitor 16 may include a parent, guardian, family member, friend, parole officer, court appointed supervisor, sobriety coach, sober buddy, sober companion, police department, or other supervisory care person, group, or authority.

Ideally the entire test and user identification process should take less than 60 seconds. The receiving station 14, for example, a monitoring station, website or server, can automatically evaluate the content signal 11 and maintain a history of the test time, result and the user identification data for each test. The receiving station 14 can also include a database and software for analysis of user identification data to confirm or reject the test results and to determine whether corrective action is required. As explained below, positive identification of the user in association with the content signal 11 may be accomplished by one or more recognition techniques including: facial recognition, voice recognition, DNA recognition, iris recognition, fingerprint recognition, a visible indicia described herein, or other recognition techniques now known or developed hereafter. Additionally, a supervisor may compare the received user identification data with a stored user identification reference in order to positively identify the user.

In some embodiments, the supervisor may also receive a photograph and/or video of the user using the testing device while the test was in progress, showing one or more visible identification indicia displayed on the testing device. The photograph and/or video may be received from a mobile device executing an app associated with the testing device. The supervisor may compare the photograph and/or video showing the one or more visible identification indicia with a reported and/or stored visible user identification indicia in order to positively identify the user.

The monitoring station can also provide a variety of reports of the user's testing history or individual test results and still frame photographs or movies used in identification of the user, to allow comprehensive and detailed analysis of the user's testing history, which can be accessed via the Internet as desired. The generated reports may be official Department of Transportation Evidential Breath Testing (EBT) reports, or may be of any other custom or preset format.

It will be appreciated that additional user identification may occur independent of the receiving station 14. For example, a user identification module of the testing device 10 may include a memory that may store a reference user identification data for comparison with the generated user identification data. Upon successful comparison, i.e. the actual user is the intended user, the user identification module may communicate a pass signal which may be added to the content signal 11.

It will be appreciated, that while at least one embodiment is herein described for testing of alcohol use, such embodiments may be equally applicable to testing for the use of controlled substances or other narcotics, as described herein.

As previously described, the testing device 10 may include a breathalyzer type device, such as a removable breath tester tip configured to be placed at or in a user's mouth during breath testing, an LED 52 and/or an LCD 54. The removable breath tester tip may be removably mounted to an end of an extension portion, which is in turn connected to a breath analysis and processing portion of the testing device 10. The LED 52 and/or LCD 54 may be suitably configured in the rear of the testing device 10 to display visible identification indicia in synchronization with the testing of the user's breath to provide identification information for later use in positive identification of the user with the test results.

In some embodiments, the breath testing sensor of the testing device 10 includes a sensor capable of detecting the presence of at least one controlled substance or narcotic. The sensor may utilize, for example, a chromatography sensors, mass spectroscopy sensors, fiber optic fluorescent sensors, or surface acoustic wave sensors to detect the presence of controlled substances or narcotics and their derivatives, such as, for example: methamphetamines, amphetamines, barbituates, tetrahydrocannabinol or other cannibanoids, benzoylmethylecgonine, diacetylmorphine or other opiates/opioids, lysergic acid diethylamide, psilocin, phencyclidine and the like, in a user's breath.

The testing device 10 may also include a PCB assembly. The PCB assembly is configured to receive the substance information and generate a breath test signal 11 therefrom. The PCB assembly is also configured to receive randomly generated visible identification data and to generate the breath test signal from the compressed identification data and the substance information. In some embodiments, the PCB is configured to operate a compression process to compress the user identification data.

Additionally, the testing device 10 may utilize software algorithms analyzing pressure and temperature sensor data to ensure that the breath being analyzed is that of a person. Accordingly, the testing device may comprise one or more pressure gauges (not shown) and/or temperature sensors (not shown) at various positions.

In some embodiments, the testing device 10 may be connected to a mobile wireless or cellular transmitter or transceiver device, which may be connected to the testing device 10 either directly, such as by an electrical connection, or wirelessly, to receive the breath test signal 11 including breath test data, fingerprint data, photograph, movie, or other user identification data, as well as any GPS location data.

In some embodiments, the testing device 10 can also be usable in combination with an iPod, iPhone, or other wireless or cellular device, or any other computing device, for example, which can serve as a wireless or cellular transmitter or transceiver device, as discussed herein.

In some embodiments, the content signal 11 including at least one of: content data, user identification data, time data, and location data, can be sent directly from one mobile wireless or cellular transmitter or transceiver device to another mobile wireless or cellular transmitter or transceiver device, without storing one or more of the content data, user identification data, or location data.

The wireless or cellular receiver monitoring station 16 can be configured to receive the content signal comprising at least one of: content data, user identification data, and location data, and to indicate an alarm condition or alert a supervisory monitor either directly or via a network.

In some embodiments, the testing device 10 may also be included in a vehicle ignition interlock signal generating system. The output of the testing device 10 may be provided to enable/disable a car ignition lock based on the data received in accordance with the algorithms described above. In addition, an on-call supervisory person may be alerted, and a receiving station 16 may also receive the enable/disable signal as well as the content signal 11 described above.

Figure 4:
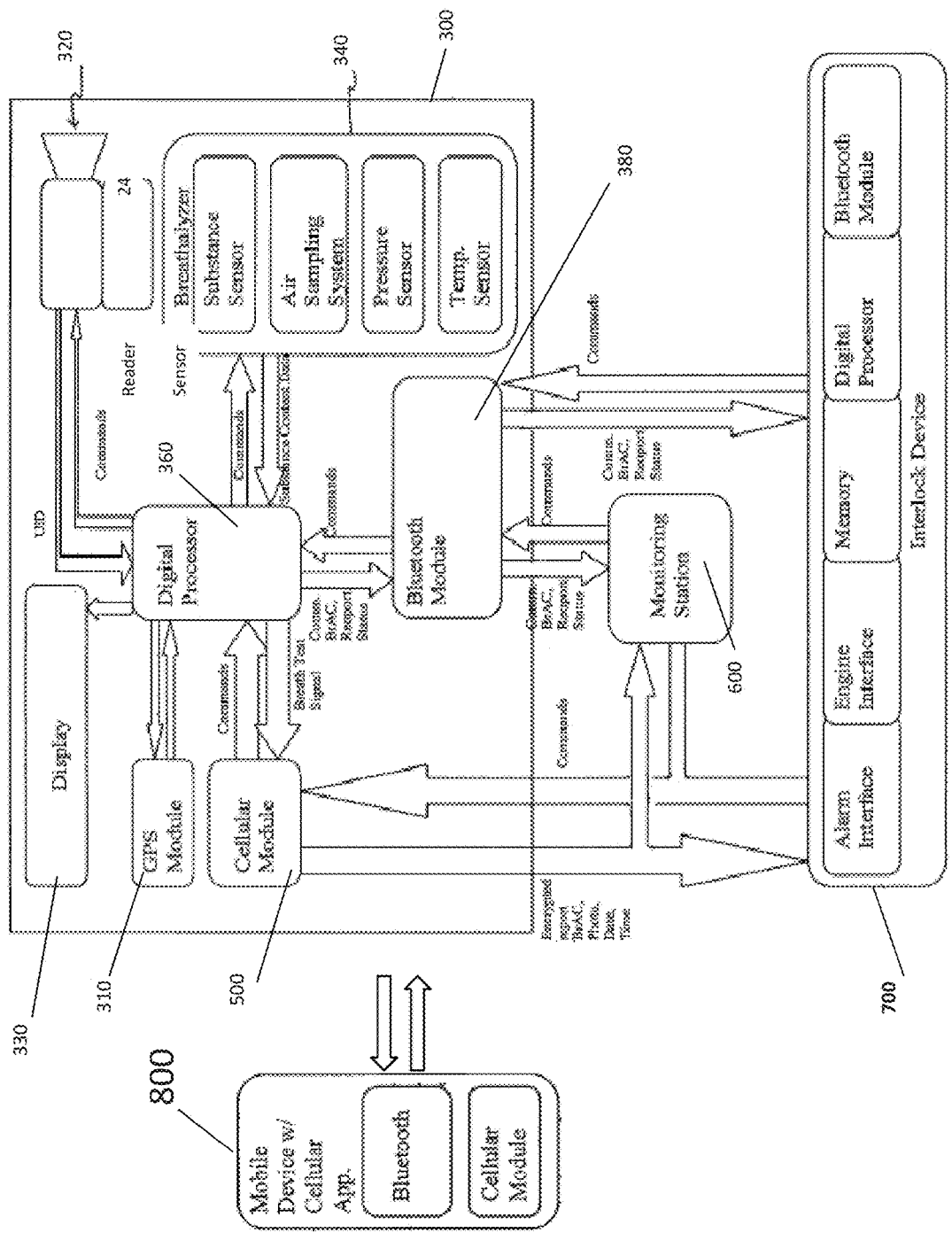
FIG. 4 illustrates another schematic diagram of a method and system for monitoring sobriety, according to an embodiment of the invention.

Referring to FIG. 4, in some embodiments, a schematic of a testing device 10 is shown. The testing device 10 in this embodiment may test for substance content. The testing device 10 may comprise an internal cell module 500. The testing device 10 in this embodiment is a stand-alone unit.

In some embodiments, the testing device 10 may include: the user identification module 320, the breath analysis module 340, the control module (CPU) 360, the cellular module 500, and a GPS module 310, and so on. The CPU 360 may randomly generate identification indicia as described herein in more detail.

The cellular module 500 may comprise a transceiver operable to transmit the breath test data to the monitoring station 600. The GPS module 310 may enable the tracking of the testing device 10 by the generation of location data. A breath test signal may be generated, at least in part, by the location data.

The testing device 10 may also comprise a personal area network ("PAN") module 380, enabling the testing device 10 to be in PAN communication with the monitoring station 600, for example, a vehicle interlock 700. Communication between the PAN and the monitoring station may be secured by data encryption techniques now known or hereafter devised. For example, data may be encrypted using a random security PIN. Devices that are compromised may be forced from the monitoring station server and may require re-activation and authentication.

The testing device 10 may also include a graphical user interface 330 ("GUI"). The GUI 330 may permit the user to interactively control the breath testing process, calibrate the testing device, schedule breath test times, retrieve past breath test reports, and/or access other information stored in the testing device 10. The GUI 330 may also permit the display of one or more visible identification indicia.

The GUI may be configured to display a reminder at a predetermined time, the reminder reminding the user that a breath testing session is due. Additionally, the testing device may cause users to receive electronic reminders via SMS, email, or bi-directional communication between the testing device and receiving station. Additionally, the testing device 10 may enable the user to receive breath test requests from the monitoring station. Such requests may be remotely or directly transmitted to the testing device 10. Such requests may also be randomly timed.

The testing device 10 may also include an audio means, such as a speaker, for generating an audio reminder that a breath testing session is due. The tone and/or duration of the audio alert may indicate the urgency of the required breath testing session. For example, three beeps may indicate a session is required immediately, while one been may indicate a session will be due shortly. The audio means may also be configured to generate a vibration reminder according to methods known in the art.

In some embodiments, the testing device 10 can also be usable in combination with an mobile device 800, such as a smart phone, a tablet, a smart watch, or other wireless or cellular device, or any other computing device. The mobile device 800 is preferably configured to be connected to the testing device 10 either directly, such as by an electrical connection, or wirelessly, such as via a Bluetooth connection, for example, to receive the breath test signal 11 and user identification data from the testing device 10. As described herein, the testing device 10 may communicate with the mobile device 800 while the test is in progress, and the mobile device 800 takes a photograph of the user.

Figure 5:
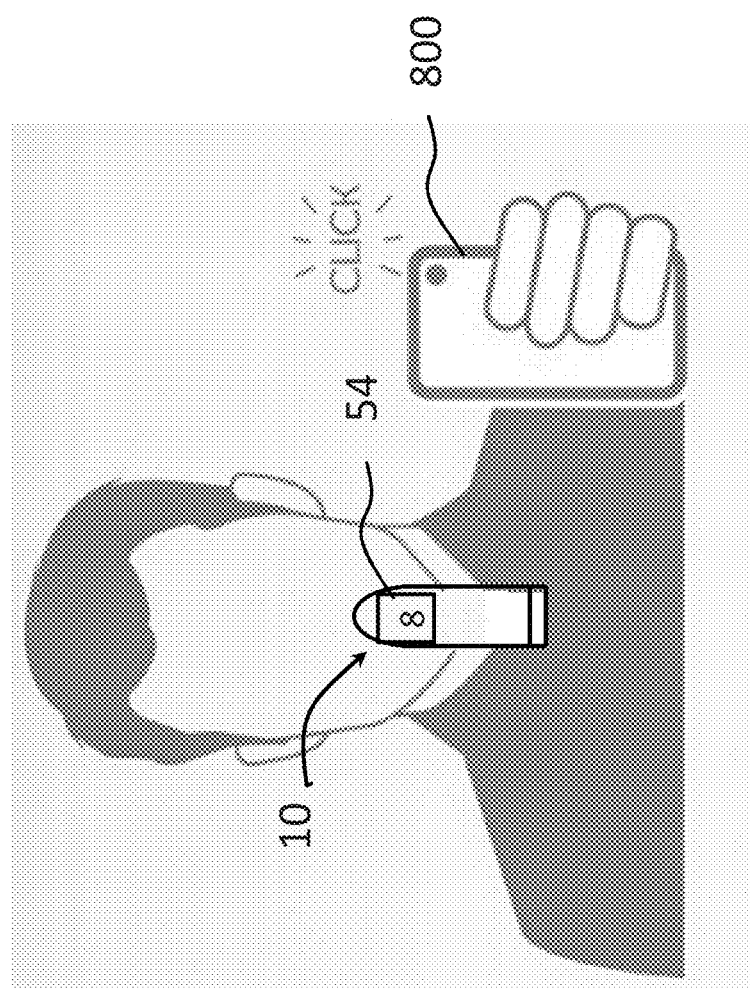
FIG. 5 illustrates an exemplary operation of a system for monitoring sobriety, according to an embodiment of the invention.
Figure 6:
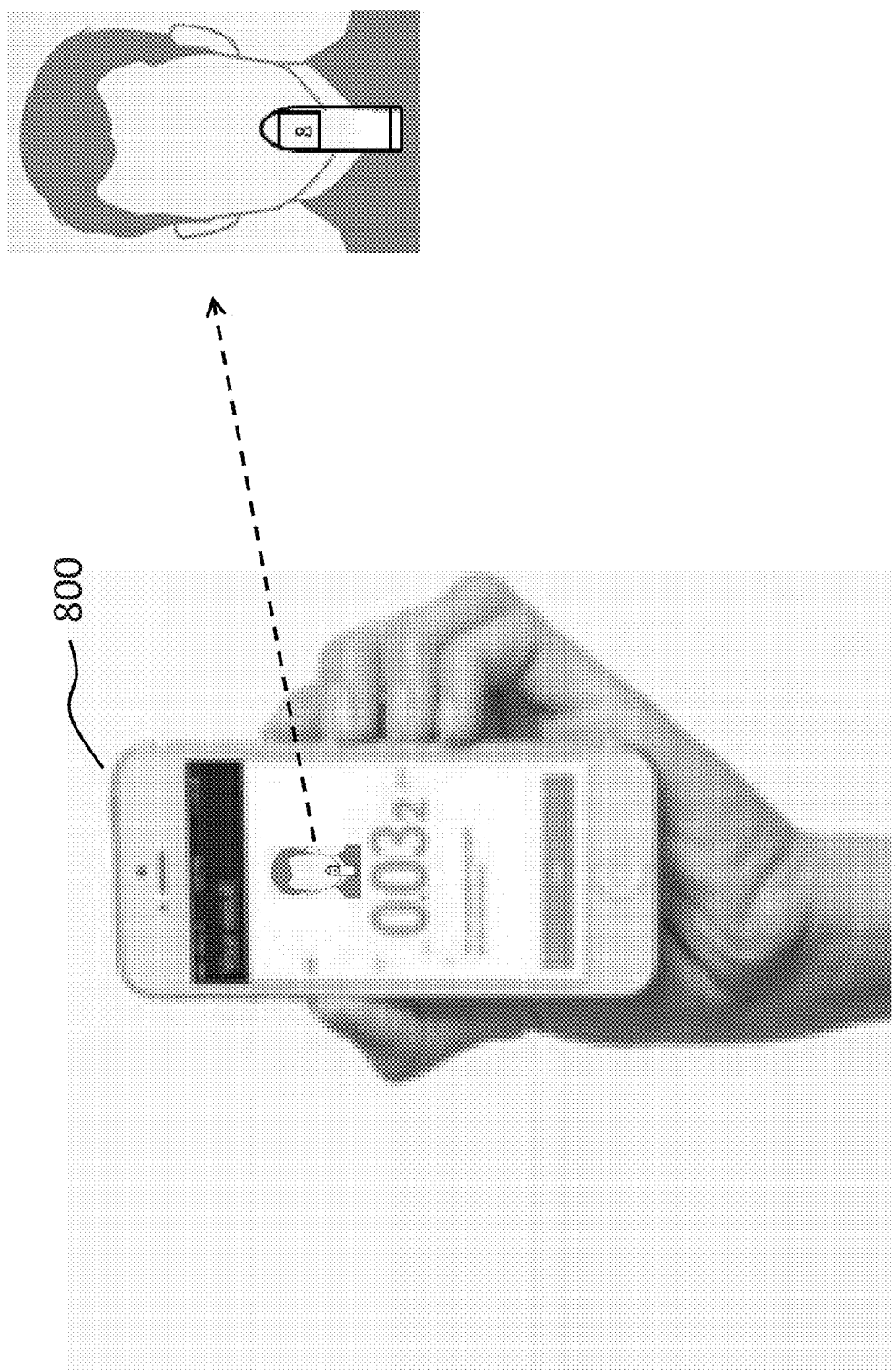
FIG. 6 illustrates an exemplary operation of a system for monitoring sobriety, according to an embodiment of the invention.

Referring to FIGS. 5 and 6, an exemplary operation of a testing device 10 is shown. As described herein, a user of the testing device 10 may also have a mobile device 800 installed with an app associated with the testing device 10. The mobile device 800 may be wirelessly connected to the testing device 10, for example, via Bluetooth. While the user blows into the testing device 10 and the test of the user's BAC is in progress, the mobile device 800 takes a photograph of the user. As shown in the example in FIG. 5, the user holds the mobile device 800 in a manner similar to one taking a self or "selfie" picture, such that the mobile device 800 can take the photograph of the user. In some embodiments, the app associated with the testing device 10 initiates and/or controls the process of taking the photograph. While the test is in progress, the testing device 10 also randomly generates a visible identification indicia, for example, shown as the randomly generated number 8 in FIG. 5. The randomly generated visible identification indicia (e.g., number 8) is displayed in the LCD 54. As such, the photograph P taken by the mobile device 800 includes the randomly generated number 8, as shown in FIG. 6, as the visible identification indicia. When the test completes, the testing device 10 sends to the mobile device 800 the BAC of the user, for example, shown as 0.032 in FIG. 6. As a result, both the BAC and the photograph P of the user may be displayed at the mobile device 800. In some embodiments, the photograph P may also be sent to a monitoring station. As described herein, the randomly generated identification indicia may be included in the substance content signal 11 as user identification data. In order to positively verify that the user of the testing device 10 is the actual user in the captured photograph, the visible identification indicia, for example, the randomly generated number 8 captured in the photograph must match the user identification indicia recorded with the substance content signal 11.

Other exemplary embodiments and processes of the testing device 10 are further described in the references mentioned above and are incorporated in entirety by reference herein.

The embodiments described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. A system for monitoring the sobriety of a user comprising:
    a testing device that generates a substance content signal and comprising a mouthpiece and a user identification device;
    wherein the user identification device generates user identification data in response to a user's breath and transmits it from the testing device to a monitoring station, and the testing device further comprises at least one of a LCD screen or a light-emitting diode LED, wherein the at least one of the LED or LCD generates and displays at least one randomly generated visible identification indicia which is one of a random number, a random color, and a random color scheme; and
    wherein the substance content signal comprises at least one substance information and at least one user identification data.

2. The system of claim 1, wherein the testing device comprises a user identification module, a breath analysis module, a control module, a cellular module, and a GPS module.

3. A system for communicating the sobriety of a user comprising:
    a testing device that generates a substance content signal comprising a mouthpiece and a user identification device, wherein the substance content signal comprises at least one substance information, wherein the user identification device generates user identification data in response to a user's breath and transmits it from the testing device to a monitoring station, and wherein the testing device further comprises at least one of a LCD screen or a LED;
    a transceiver unit configured to transmit the substance content signal to a receiving station, wherein the receiving station comprises any location, device, or system where the substance content signal is received;
    a supervisory monitor; and
    wherein the receiving station automatically tests the substance content signal and maintains a history of the test time, result, and the user identification data for each test, and further wherein the receiving station comprises a database and a software for analyzing user identification data to confirm or reject the test results.

* * * * *